United States Patent [19]

Nubel et al.

[11] Patent Number: 5,087,779
[45] Date of Patent: Feb. 11, 1992

[54] HYDROCARBON HALOGENATION

[75] Inventors: Philip O. Nubel, Naperville; Larry C. Satek, Wheaton; Michael J. Spangler, Sandwich; Glenn O. Michaels, South Holland, all of Ill.

[73] Assignee: Amoco Corporation, Chicago, Ill.

[21] Appl. No.: 514,172

[22] Filed: Apr. 25, 1990

[51] Int. Cl.$^5$ ............................................. C07C 17/154
[52] U.S. Cl. ..................................... 570/245; 570/169
[58] Field of Search ................................. 570/245, 169

[56] References Cited

U.S. PATENT DOCUMENTS

| | | | |
|---|---|---|---|
| 3,856,705 | 1/1974 | McArthur | 518/715 |
| 4,052,468 | 10/1977 | Peterson et al. | |
| 4,052,470 | 10/1977 | Nychka et al. | |
| 4,060,555 | 11/1977 | Peterson et al. | |
| 4,105,691 | 8/1978 | Sweeney et al. | |
| 5,001,293 | 3/1991 | Nubel et al. | |

FOREIGN PATENT DOCUMENTS 0117731 9/1984 European Pat. Off. .

Primary Examiner—Howard T. Mars
Attorney, Agent, or Firm—Nick C. Kottis; William H. Magidson; Ralph C. Medhurst

[57] ABSTRACT

A method for halogenating hydrocarbons wherein a reaction mixture including a hydrocarbon-containing feed, a hydrogen halide and an oxygen-containing gas is contacted at appropriate reaction conditions with a catalyst of copper aluminum borate to form halogenated hydrocarbons.

30 Claims, No Drawings

HYDROCARBON HALOGENATION

BACKGROUND OF THE INVENTION

This invention relates generally to hydrocarbon conversion and, more specifically, to the catalytic halogenation of hydrocarbons.

As the uncertain nature of ready supplies and access to crude oil has become increasingly apparent, alternative sources of hydrocarbons and fuel have been sought out and explored. The conversion of low molecular weight alkanes (lower alkanes) to higher molecular weight hydrocarbons has received increasing consideration as such low molecular weight alkanes are generally available from readily secured and reliable sources. Natural gas, partially as a result of its comparative abundance, has received a large measure of the attention focused on sources of low molecular weight alkanes. Large deposits of natural gas, mainly composed of methane, are found in many locations throughout the world. In addition, low molecular weight alkanes are generally present in coal deposits and may be formed during numerous mining operations, in various petroleum processes, and in the above- or below-ground gasification or liquefaction of synthetic fuelstocks, such as coal, tar sands, oil shale and biomass, for example. In addition, in the search for petroleum, large amounts of natural gas are discovered in remote areas where there is no local market for its use as a fuel or otherwise. Additional major natural gas resources are prevalent in many remote portions of the world such as remote areas of western Canada, Australia, U.S.S.R. and Asia. Commonly, natural gas from these types of resources is referred to as "remote gas".

Generally, much of the readily accessible natural gas is used in local markets as the natural gas has a high value use as a fuel whether in residential, commercial or industrial applications. Accessibility, however, is a major obstacle to the effective and extensive use of remote gas. In fact, vast quantities of natural gas are often flared, particularly in remote areas from where its transport in gaseous form is practically impossible.

Conversion of natural gas to liquid products is a promising solution to the problem of transporting low molecular weight hydrocarbons from remote areas and constitutes a special challenge to the petrochemical and energy industries. The dominant technology now employed for utilizing remote natural gas involves its conversion to synthesis gas, also commonly referred to as "syngas", a mixture of hydrogen and carbon monoxide, with the syngas subsequently being converted to liquid products. While syngas processing provides a means for converting natural gas to a more easily transportable liquid that in turn can be converted to useful products, the intermediate step involved is such processing, i.e., the formation of the synthesis gas, is typically relatively costly as it involves adding oxygen to the rather inert methane molecule to form a mixture of hydrogen and carbon monoxide. While oxygen addition to the carbon and hydrogen of methane molecules may be advantageous when the desired products are themselves oxygen containing, such as methanol or acetic acid, for example, such oxygen addition is generally undesirable when hydrocarbons such as gasoline or diesel fuel are the desired products as the added oxygen must subsequently be removed. Such addition and removal of oxygen naturally tends to increase the cost involved in such processing.

Methane, the predominant component of natural gas, although difficult to activate, can be reacted with oxygen or oxygen-containing compounds such as water or carbon dioxide to produce synthesis gas. Synthesis gas can be converted to syncrude such as with Fischer-Tropsch technology and then upgraded to transportation fuels using usual refining methods. Alternatively, synthesis gas can be converted to liquid oxygenates which in turn can be converted to more conventional transportation fuels via catalysts such as certain zeolites.

Because synthesis gas processing requires high capital investment, with the syngas being produced in relatively energy intensive ways, such as by steam reforming where fuel is burned to supply heat for reforming, and represents an indirect route to the production of hydrocarbons, the search for alternate means of converting methane directly to higher hydrocarbons continues.

One such alternative method involves methane conversion to higher hydrocarbons via a "chlorine-assisted" route, such as represented by the following 2-step process:

$$CH_4 + HCl + O_2 \rightarrow \text{chloromethanes} + H_2O \quad (1)$$

$$\text{chloromethanes} \rightarrow C_{2+} \text{hydrocarbons} + HCl \quad (2)$$

In the first step of such a process, methane (using HCl and oxygen) is chlorinated to chloromethanes. Such a chlorination step is also referred to as methane "oxychlorination" or "oxyhydrochlorination".

In the second step of such a process, chloromethanes are converted to higher hydrocarbons, e.g., hydrocarbons having 2 or more carbon atoms, represented by "$C_{2+}$", and HCl. The HCl generated in the second step can be recycled back to the first step so that effectively there is no net consumption of chlorine in the overall process.

Such a chlorine-assisted process is not yet practiced commercially.

Catalysts for the chlorination of the hydrocarbons, such as methane, have in the past typically consisted of copper chloride and promoters such as potassium and lanthanum chlorides supported on silica or alumina. For example, see *Applied Catalysis*, Vol. 11, pp. 35-71 (1984); *J. Catalysis*, Vol. 99, pp. 12-18 (1986); European Patent Application 0117731, filed Sept. 5, 1984, by British Petroleum; and U.S. Pat. No. 4,123,389 issued Oct. 31, 1978, and assigned to Allied Chemical Corporation.

The role of the potassium and/or lanthanum chloride promoter in such catalysts is not fully understood. It is believed that the presence of such a promoter results in the formation of a supported eutectic mixture of the copper chloride and promoter chloride, which mixture is molten at reaction temperatures. Catalytic activity is believed to be facilitated by the enhanced mass transfer properties of a molten phase relative to a similar composition in a solid phase.

Generally, while such catalysts initially appear relatively active and selective, the use of such catalysts suffers from relatively rapid catalyst deactivation realized during such use of the catalyst. Such deactivation is believed to be due to changes in the active copper species of the catalyst with time as the catalyst is on stream.

In addition, U.S. Pat. Nos. 4,052,468; 4,052,470; 4,060,555; and 4,105,691, all assigned to Allied Chemical Corporation, relate to processes for the production of chlorofluorinated hydrocarbons, such as cycloaliphatic, acyclic, aliphatic ketones and carboxylic acids, respectively, via the use of a Deacon catalyst (such as a metal halide impregnated on a suitable carrier).

Noceti, et al., U.S. Pat. No. 4,769,504, discloses a process for the production of aromatic-rich, gasoline boiling range hydrocarbons from lower alkanes, particularly from methane. The process is carried out in two stages. In the first stage, an alkane is reacted with oxygen and hydrogen chloride over an oxyhydrochlorination catalyst such as copper chloride with minor proportions of potassium chloride and rare earth chloride. This produces an intermediate gaseous mixture containing water and chlorinated alkanes. In the second stage, the chlorinated alkanes are subsequently contacted with a crystalline aluminosilicate catalyst in the hydrogen or metal promoted form to produce gasoline range hydrocarbons with a high proportion of aromatics and a small percentage of light hydrocarbons ($C_2$-$C_4$). The light hydrocarbons can be recycled for further processing over the oxyhydrochlorination catalyst.

The search for a long-lived catalyst effective in catalyzing the halogenation, particularly the chlorination, of hydrocarbons, particularly lower hydrocarbons, especially methane, has continued.

Catalytically active copper aluminum borate is the subject of commonly assigned Satek U.S. Pat. No. 4,590,324; of commonly assigned Kouba, et al., U.S. Pat. No. 4,613,707; of commonly assigned Zletz, et al., U.S. Pat. No. 4,645,753; of commonly assigned Zletz, U.S. Pat. No. 4,729,979; of commonly assigned De Simone, et al., U.S. Pat. No. 4,755,497; and of commonly assigned copending application Zletz, U.S. Ser. No. 285,103 filed Dec. 14, 1988. These patents and application disclose the preparation, characterization and utility of copper aluminum borate and are hereby incorporated by reference. None of these patents, however, disclose or suggest the use of crystalline copper aluminum borate in a process for the halogenation and, in particular, the chlorination of hydrocarbons.

Further, McArthur, in U.S. Pat. Nos. 3,856,702, 3,856,705 and 4,024,171, discloses that it has been long the practice in the art to impregnate or otherwise distribute active catalytic metals support materials having desired properties of porosity, surface area, thermal and mechanical stability, and suitably inert chemical properties. McArthur teaches that a superior catalyst support results from calcining certain alumina and boria composites within the temperature range of about 1,250° F.-2,600° F., which appears to produce a defined crystalline phase of $9\ Al_2O_3 \cdot 2B_2O_3$, following which the aluminum borate support can be impregnated with solution(s) of desired catalytic salt or salts, preferably those that are thermally decomposable to give the corresponding metal oxides. Following impregnation, the finished catalysts are dried and, if desired, calcined at temperatures of 500° to 1000° F., for example. In the final catalyst, the active metal or metals may appear in the free form as oxides or sulfides or in another active form. Examples 1 to 6 of McArthur impregnate the calcined support with an aqueous solution of copper nitrate and cobalt nitrate to provide about 4% copper as CuO and 12% cobalt as $Co_2O_3$ in the final catalyst.

Uhlig, in Diplomarbeit, Institute for Crystallography, Aacken (October 1976) "Phasen - und Mischkristall - Bildung im $B_2O_3$ - armeren Teil des Systems $Al_2O_3$-CuO-$B_2O_3$" ("Formation of Phases and Mixed Crystals in that Part of the $Al_2O_3$-CuO-$B_2O_3$ System With a Low $B_2O_3$ Content") which is hereby incorporated by reference, discloses preparation of a green tetragonal solid copper aluminum borate having the structure $Cu_2Al_6B_4O_{17}$ by grinding together solid boron oxide, copper oxide and alumina, sealing the ground metal oxides in a platinum tube and heating same at 1000° C. for a period of 48 hours. Attempts to produce this copper aluminum borate by the indicated route yield well-defined, dense crystalline particles which have an extremely low surface area and are accordingly not suitable for many catalysis processes due to the low porosity and surface area.

Also, Asano, U.S. Pat. No. 3,971,735, discloses a copper-, zinc-, aluminum- and boron-containing catalyst useful in low temperature methanol synthesis. The catalyst is preferably produced by forming a mixture of water-soluble salts of copper, zinc and boron, precipitating same with an alkali carbonate and mixing with alumina. The catalyst is then fired at approximately 300°-450° C.

SUMMARY OF THE INVENTION

It is an object of the present invention to overcome one or more of the problems described above.

According to the invention, a method for halogenating hydrocarbons is provided wherein a reaction mixture including a hydrocarbon-containing feed, a hydrogen halide, and an oxygen-containing gas are contacted with a catalyst of crystalline copper aluminum borate at appropriate reaction conditions to produce halogenated hydrocarbons.

In one embodiment of the invention, a method for chlorinating hydrocarbons is provided which includes the step of contacting a reaction mixture including a hydrocarbon-containing feed, HCl, and an oxygen-containing gas with a catalyst of crystalline copper aluminum borate, having a specified X-ray diffraction pattern, under appropriate reaction conditions to form chlorinated hydrocarbons.

The invention also provides a method for chlorinating methane to form chloromethane. In such a method, a reaction mixture containing methane, HCl, and an oxygen-containing gas is contacted with a catalyst of crystalline copper aluminum borate and a promoting amount of alkali metal compound, under appropriate reaction conditions, to form chloromethane. In such a method, the crystalline copper aluminum borate has a specified X-ray diffraction pattern and a surface area in the range of about 0.1 to about 300 $m^2/g$.

Also the invention provides a method for chlorinating $C_2$ hydrocarbons. Such a method includes the step of contacting a reaction mixture which includes $C_2$ hydrocarbons, HCl and an oxygen-containing gas with a catalyst of copper aluminum borate, having a specified X-ray diffraction pattern and surface area in the range of about 0.1 to about 300 $m^2/g$, under appropriate reaction conditions, to form a product mixture including dichloroethane.

Other objects and advantages of the invention will be apparent to those skilled in the art from the following detailed description taken in conjunction with the appended claims.

DETAILED DESCRIPTION OF THE INVENTION

The present invention provides a novel method of halogenating hydrocarbons.

While the process of the invention is described hereinafter with particular reference to the chlorination of methane, it will be apparent that the process also has application in the chlorination of other hydrocarbons such as $C_2$ hydrocarbons such as ethane, ethylene, acetylene, as well as aromatics such as benzene, toluene, ethylbenzene, chlorobenzene, naphthalene, xylenes, etc., for example. The process of the invention is believed to also have applicability to hydrocarbon halogenation using other halogen elements (fluorine, bromine and iodine), in particular bromine. It is to be understood, however, that at the present time the invention is perceived to have particular utility in the chlorination of lower hydrocarbons such as $C_1$ and $C_2$ hydrocarbons and especially in the chlorination of lower alkanes, such as methane, as such chlorinated lower hydrocarbons can serve as a relatively highly reactive feedstock for further processing.

In the chlorination of methane in accordance with the invention, a reaction mixture including methane, HCl and an oxygen-containing gas, such as pure oxygen, air, or oxygen-enriched air, for example, is contacted with a catalyst of crystalline copper aluminum borate at appropriate reaction conditions to form chloromethane products such as methylchloride, dichloromethane, chloroform, carbon tetrachloride, or various mixtures of these.

Such catalytic chlorination of methane can be performed at reaction temperatures of about 100° C. to about 700° C., preferably at reaction temperatures of about 250° C. to about 500° C. In addition, the pressure at which the process is effected is not, within reasonable bounds such as operation at from about 10 psia to about 2000 psia, believed critical and may be selected in view of overall processing economics and schemes. Also, while the process will be described hereinafter with reference to general operation in a continuous mode operation, with a Gas Hourly Space Velocity (GHSV), defined as the volume of reactant gas at STP per volume of catalyst per hour, for continuous operation suitably being in the range from about 1 to about 10,000 volume per volume per hour and a reactant-catalyst contact time being in the range of about 0.1 second to about 100 seconds, it is to be understood that the process can be performed in a batch-type mode of operation, if desired.

As described above, the oxygen-containing gas as used in the practice of the invention can be pure oxygen, air, or oxygen-enriched air, for example. Thus, the oxygen-containing gas can contain diluents such as the inert gases, nitrogen, helium, argon, etc., as well as diluents, such as carbon dioxide, which are generally inert under the subject reaction conditions. The oxygen-containing gas will, however, preferably contain at least 1 volume percent oxygen.

Further, the components of the reaction mixture, i.e., methane, HCl, and an oxygen-containing gas, can be employed in any desired effective ratio. Suitable ratios of C:Cl:O are best determined experimentally. Typically, the ratio of carbon atoms to chlorine atoms to oxygen atoms will be in the range of about 10:0.1–100:0-.1–100 and preferably 10:1–50:1–50, with the selection of an appropriate operating ratio typically influenced by factors such as desired methane conversion, desired chlorocarbon product, etc. For example, in the chlorination of methane, if conversion of relatively greater amounts of methane are desired, then relatively greater amounts of HCl and oxygen may preferably be employed. Further, if a high reaction selectivity to monochloromethane products, as opposed to higher chlorinated methane products, e.g., dichloromethane, trichloromethane, and tetrachloromethane, is desired then relatively lower amounts of HCl and oxygen may preferably be employed. Also, use of methane in relative amounts in excess of the stoichiometric amounts required for the formation of the desired chlorocarbon product generally results in the production of relatively smaller, or minor, amounts of carbon oxides ($CO_x$), i.e., CO and $CO_2$. Reduction in carbon oxide production is generally preferred when seeking to minimize carbon atom loss to undesired products (e.g., in chlorocarbon formation in which carbon oxide formation is undesired, it will generally be preferred to employ methane in a relative amount in excess of the stoichiometric amount required in the desired chlorocarbon).

In addition, the reaction mixture may also contain other components such as other hydrocarbons, oxygenated hydrocarbons (e.g., alcohols, ketones, etc.), halocarbons, water, chlorine ($Cl_2$), carbon oxides (CO and/or $CO_2$), and inert gases such as nitrogen, helium, argon, etc.

The catalysts employed in the practice of the invention are crystalline copper aluminum borates, e.g., crystalline copper-aluminum-boron mixed oxide materials, such as described in the previously identified patents and patent application.

Neat copper aluminum borate having the empirical formula $Cu_2Al_6B_4O_{17}$ is a crystalline compound, green in color. For catalytic studies, neat copper aluminum borate is generally prepared as a microcrystalline material. The crystal structure of the material has been determined by neutron and X-ray powder diffraction methods as well as by single crystal X-ray diffraction to obtain a precise description of the structure. Neat copper aluminum borate crystallizes in the tetragonal space group I4/m with a=10.5736(7) Angstroms and c=5.6703(6) Angstroms. The structure contains edge sharing chains of octahedral Al atoms parallel to the c-axis. These planes are joined in the a-axis and b-axis directions by trigonal planar $BO_3$ groups. The unit cell contains trigonal bipyramidal sites, randomly equally occupied by either Cu or Al atoms, which share a face with the Al atom octahedron. These trigonal bipyramidal sites share equatorial corners at a square planar O atom. The structure also contains 8 ring channels parallel t the c-axis and approximately 4 Angstroms in diameter.

The catalysts for use in the practice of the present invention may be prepared by various methods, including the solid-state preparation technique described in DeSimone, et al., U.S. Pat. No. 4,755,497, issued July 5, 1988, the disclosure of which is hereby incorporated herein by reference, but preferably is prepared by the technique described in the pending application, Satek, U.S. Ser. No. 361,278, filed June 5, 1989, the disclosure of which is hereby incorporated by reference.

In such a process for producing copper aluminum borate, a homogeneous gel is formed of an aqueous-organic medium comprising a volatile organic liquid having at least partial miscibility with water. Useful volatile organic compounds will typically have normal boiling points in a temperature range downward from about 140° C. Suitable organic compounds include alcohols, ethers, aldehydes and ketones having from about 1 to about 5 carbon atoms per molecule, such as methanol, ethanol, 2-propanol, 2-butanol, 2-methyl-2-propanol, 2-propen-1-ol, methoxymethane, methoxyethane, 1-methoxypropane, 2-methoxypropane, 2-ethoxypropane, 1,3-dioxane, 1,4-dioxane, propanone, butanone, 3-pentanone, and 2-pentanone, and N,N-dimethylformamide. Of these organic compounds, methanol, ethanol, and N,N-dimethylformamide are preferred.

Advantageously, the amounts of water and volatile organic liquid used are the least amounts needed to consistently obtain a homogeneous copper aluminum borate precursor. Likewise, suitable ratios of organic liquid to water for each liquid system are best determined experimentally. Typically, the ratios of organic liquid to water by volume are less than about 1, preferably in a range from about 0.01 to about 0.99, more preferably in a range from about 0.1 to about 0.9.

More specifically, the method for producing a copper aluminum borate precursor comprises forming an aqueous composition comprising a source of copper(II) ions, a source of alumina, and a source of boria, admixing with the aqueous composition a volatile organic liquid containing a chemical base to form a homogeneous gel which, when dried to form a superficially dry solid and/or calcined to a sufficiently high temperature, forms crystalline copper aluminum borate.

A sol or any reasonably soluble salt of copper(II) ions or precursor thereof, which is at least partially soluble in the dispersing liquid, such as the acetate, formate, nitrate, carbonate, chloride, and the like, can be a suitable source of copper for use in this catalytic composition. Salts of copper(II) such as copper(II) nitrate, copper(II) acetate, copper(II) carbonate, etc. are preferred. Copper(II) nitrate is preferred as it behaves well in air drying. When the source of copper(II) is a sol, oxides are preferred.

Typically, best results are obtained when each of the sources used is chosen to reduce the content of foreign anions and cations in the reaction mix.

The source of alumina can be any material capable of producing alumina, such as aluminum nitrate, aluminum acetate, aluminum borate, etc. It is preferred, however, that the source of alumina be a well-dispersed liquid, such as an alumina sol.

The source of boria is a material such as borate or boric acid with pure boric acid being preferred.

Generally, these components can be combined in an aqueous or aqueous-organic medium in approximately stoichiometric proportions sufficient to provide copper aluminum borate having the mixed metal oxide formula $2CuO \cdot 3Al_2O_3 \cdot 2B_2O_3$ or the empirical formula $Cu_2Al_6B_4O_{17}$.

Typically, the mole ratios of the various reactants can be varied to produce the copper aluminum borate by this method. Specifically, the mole ratios in terms of oxides of the initial reactant concentrations are characterized by the general mixed oxide formula

$$(x)CuO \cdot (y)Al_2O_3 \cdot (z)B_2O_3$$

wherein x, y and z are numbers representing molar amounts of the oxides of the source reagents.

The mole ratios of $CuO/B_2O_3$, calculated as x/z, are about 0.1 to about 20, preferably about 0.15 to about 10, and most preferably about 0.25 to about 6, and the mole ratios of $Al_2O_3/B_2O_3$, calculated as y/z, are from about 0.1 to about 20, preferably about 0.15 to about 10, and more preferably about 0.25 to about 6.

In somewhat greater detail, a preferred preparation procedure is to dissolve the boria source and disperse the alumina source in water or a volatile organic liquid and water by mixing in a blender for about 3-5 minutes and then adding an aqueous sol or solution of a source of copper(II) to the blender followed by gelation by admixing with the aqueous mixture a volatile, organic liquid, preferably methanol, ethanol, or N,N-dimethylformamide, containing a basic chemical compound.

Suitable basic compounds include oxides, hydroxides and salts of alkali metal elements, ammonium hydroxide, and hydroxides of organic cations, such as methylammonium hydroxide or tetramethylammonium hydroxide. Preferred basic chemical compounds comprise at least one quaternary ammonium cation selected from the group consisting of tetramethylammonium, tetraethylammonium, benzyltrimethylammonium, trimethyl-n-octylammonium, dibenzyldimethylammonium, and cetyltrimethylammonium. The presence of the ammonia as well as other volatile components in the gelled mixture, such as acetate ion, nitrate ion, etc., is advantageous in providing the final calcined solid with sufficiently high surface area and porosity desirable for catalytic reactions.

Typically, the pH of the aqueous mixture is in a range from about 4 to about 12. If the reaction media is too acidic or too basic, the desired solid generally will not form, or other contaminating phases are formed in addition to the desired product. To some extent the pH of the reaction mixture controls surface properties of the final calcined solid material. Preferably, the pH of the reaction mixture is in a range from about 5 to about 9, more preferably about 5.5 to about 8, in order to gel the reaction mixture.

The gelled mixture is mildly dried, such as for a period of time ranging from a few hours to a few days at varying temperatures, typically about 20° to about 225° C., to form a dry cake which is a copper aluminum borate precursor. Advantageously, the gelled mixture is allowed to air-dry, usually for about 1-3 days, followed by vacuum drying, typically at a pressure of about 0.3 atmosphere for about 15 to 25 hours at about 100° C. to 150° C. with a purge of dry gas, such as nitrogen.

The superficially dry precursor is calcined, preferably at a temperature within the range of about 650° to about 1000° C. for a reaction time that is sufficient to effect formation of crystalline copper aluminum borate, typically a reaction time within the range of about 2 to about 3 hours. Samples of material can be removed during calcination to check the degree of crystallization and determine the optimum calcination time.

The crystalline material formed can be crushed to a powder or to small particles and extruded, pelletized, or made into other forms suitable for its intended use. In a preferred embodiment of the above-described method, the crystalline material formed can be washed with a solvent, preferably an aqueous solvent, which removes impurities such as excess boria, without destroying the crystalline material formed, mildly dried for anywhere from a few hours to a few days at varying temperatures, typically about 50° to about 225° C., to form a dry cake which can then be treated as required for its intended use.

The dry, copper aluminum borate catalyst precursor is subsequently calcined, which calcination is usually carried out at a temperature in the range of from about 650° C. to about 900° C. and preferably at a temperature of about 700° C. to about 850° C. for about 0.1 hour to about 24 hours, and typically in air. In practice, higher calcination temperatures are typically associated with shorter calcination times.

These solid catalyst materials can be admixed with or incorporated within various binders or matrix materials if desired. They can be combined with active or inactive materials, synthetic or naturally occurring oxides, as well as inorganic or organic materials which would be useful for binding such substances. Well-known materials include silica, silica-alumina, alumina, magnesia, titania, zirconia, alumina sols, hydrated aluminas, clays such as bentonite or kaolin, Sterotex (a powdered vegetable stearine produced by Capital City Products, Co., Columbus, Ohio), or other binders well known in the art.

The X-ray diffraction patterns in Table I show the significant lines for unreduced CuAB of this invention and CuAB of Uhlig.

X-ray data were determined by standard techniques. The radiation was the K-alpha doublet of copper, and a proportional counter spectrometer with a strip chart pen recorder was used. The peak heights, I, and the positions as a function of 2 times theta, where theta is the Bragg angle, were read from the spectrometer chart. From these the relative intensities, 100 $I/I_0$, where $I_0$ is the intensity of the strongest line or peak, and d (obs.), the interplanar spacing in Angstroms, corresponding to the recorded lines, were calculated. In Table I, the relative intensities are given in terms of the symbols VVS=very very strong (>100), VS=very strong (80-100), S=strong (50-80), M=Medium (20-50), W=weak (10-20) and VW=very weak (<10).

TABLE I

| (d) Angstroms | CuAB | Uhlig CuAB |
|---|---|---|
| 7.50 ± .1 | VM-M | M |
| 5.29 ± .05 | VS | VS |
| 5.00 ± .05 | S | S |
| 4.92 ± .03 | | |
| 3.73 ± .03 | W-M | W |
| 3.64 ± .03 | VW-W | VW |
| 3.58 ± .03 | | |
| 3.35 ± .03 | W | W |
| 2.98 ± .03 | VW-W | W |
| 2.84 ± .03 | VW-W | VW |
| 2.78 ± .02 | | |
| 2.64 ± .02 | M-S | M |
| 2.61 ± .02 | W-M | W |
| 2.50 ± .02 | W-M | VW |
| 2.45 ± .02 | | |
| 2.26 ± .02 | W-M | W |
| 2.22 ± .02 | | |
| 2.16 ± .02 | M | W |
| 2.13 ± .02 | | |
| 2.07 ± .02 | M | M |
| 1.97 ± .02 | M | W-M |
| 1.91 ± .02 | | VW |
| 1.86 ± .01 | W-M | VW |
| 1.81 ± .01 | M | W |
| 1.76 ± .01 | VW | VW |
| 1.67 ± .01 | W-M | W |
| 1.60 ± .01 | W-VW | VW |
| 1.555 ± .01 | W-VW | VW |

The significant X-ray diffraction lines for copper aluminum borate are set forth below in Table A, with the symbols, e.g., VS, S, M, W, etc., for relative intensities corresponding to the previously indicated ranges.

TABLE A

| (d) Angstroms | Strength |
|---|---|
| 5.29 ± .05 | VS |
| 5.00 ± .05 | S |
| 3.73 ± .03 | W-M |
| 2.64 ± .03 | M-S |

TABLE A-continued

| (d) Angstroms | Strength |
|---|---|
| 2.61 ± .02 | W-M |
| 2.50 ± .02 | W-M |
| 2.26 ± .02 | W-M |
| 2.16 ± .02 | M |
| 2.07 ± .02 | M |
| 1.97 ± .02 | M |
| 1.86 ± .01 | W-M |
| 1.81 ± .01 | M |

It has been found that the addition of a promoting amount of an alkali metal-containing compound to such crystalline copper aluminum borates results in a catalyst having improved selectivity performance, i.e., reduction in yield by undesired carbon oxide byproducts, e.g., CO and $CO_2$. For example, the incorporation of compounds such as chlorides, oxides, for example, of alkali metals such as potassium or lithium, for example, into the copper aluminum borate catalyst results in a catalyst which yields lesser amounts of carbon oxides at equivalent conversion levels than do similar, unmodified copper aluminum borate catalysts. This effect is surprising since the copper aluminum borate materials are crystalline and not likely to form eutectic melts as do conventional copper chloride catalysts as described above. Also, in contrast to the above-described chlorination catalysts of copper chloride and promoters such as potassium and lanthanum chlorides supported on silica or alumina, compounds of other alkali metals, such as lithium, as well as alkali metals (including potassium) in nonchloride compounds, such as in the form of oxides, have proven effective in promoting catalyst selectivity. In addition, the incorporation of compounds such as hydroxides, carbonates, nitrates, bromides, iodides, sulfates, acetates, etc. of such alkali metals into the copper aluminum borate catalyst is also believed to similarly result in a catalyst which yields lesser amounts of carbon oxides at equivalent conversion levels than do similar, unmodified copper aluminum borate catalysts.

Further, the X-ray diffraction powder patterns of the used and new catalysts are nearly identical for all cases, including the potassium chloride- and potassium oxide-doped materials. This indicates, in contrast to other processes using such copper aluminum borate catalysts, that this process does not involve substantial catalyst degradation to copper metal on a matrix, currently believed to be an aluminum borate with copper ions incorporated as if in a solid solution. The used catalysts, including the potassium chloride- and potassium oxide-doped materials do, however, exhibit some incorporation of chlorine. This incorporated chlorine is dispersed throughout the catalyst particle and may be incorporated into the crystal lattice.

Such catalysis, in contrast to other catalytic processes involving the use of such copper aluminum borate, does not involve substantial catalyst degradation to copper on alumina borate.

Incorporation of the potassium compound may be performed during the catalyst preparation or afterwards by impregnation of the finished crystalline copper aluminum borate. Impregnation may be accomplished by any suitable technique, such as aqueous incipient wetness impregnation, for example. Further, if potassium oxide is desired as the modifier/promoter, impregnation with potassium carbonate or nitrate is preferred, followed by high temperature calcination to yield the supportive oxide. Other potassium compounds, including potassium acetate, hydroxide, sulfate, and chloride, are suitable for use for impregnation. Generally, the promoter-including crystalline copper aluminum borate will contain about 0.1 to about 50 weight percent of the alkali metal-containing compound and preferably will contain about 1 to about 30 weight percent of the alkali metal-containing compound.

The following examples illustrate the practice of the invention. It is to be understood that all changes and modifications that come within the spirit of the invention are desired to be protected and thus the invention is not to be construed as limited by these examples.

EXAMPLES

Example 1

A crystalline copper aluminum borate catalyst, prepared by the solid-state preparation technique of De Simone, et al., U.S. Pat. No. 4,755,497, containing a crystalline copper aluminum borate phase with a 2:3:2 $CuO:Al_2O_3:B_2O_3$ composition and, by ICP elemental analysis containing 23.3 wt. % copper, 26.6 wt. % aluminum, and 8.6 wt. % boron; and having a BET (Digisorb) surface area of 26 $m^2/g$ in 1/8 inch pellet form was ground and sieved to 20-35 mesh prior to testing for methane chlorination. This catalyst was found to have the X-ray diffraction patterns shown in Table I and the significant X-ray diffraction lines set forth in Table A, above.

Catalyst testing was performed using a fixed-bed, single-pass quartz tube flow reactor unit. The reactor was a 18 in long, 16 mm OD quartz tube with a 4 mm OD quartz center thermowell and was operated in downflow mode. Heat was supplied by a 12 in long, three-zone tube furnace. Catalyst beds were supported with alpha-alumina (30-50 mesh) and quartz wool packing materials. A catalyst charge of 5.0 g, corresponding to a 3 in bed length, was centered in the heated portion of the reactor. A pre-blended gas feed mixture consisting of 10 mol% methane, 5 mol% oxygen, 10 mol% HCl, and 75 mol% nitrogen (prepared by Matheson) was employed; feed mixture flow was controlled by a mass flow controller. All runs were performed at 1 atm reactor pressure. Reactor effluent gas and feed gas samples were analyzed by gas chromatography using a TC detector. The nitrogen in the feed mixture was employed as an internal GC standard in order to calculate conversions and selectivities.

Table II presents the results of methane chlorination runs with this crystalline copper aluminum borate catalyst.

Example 2

In a test for thermal reactions, wall effects, and activity of packing materials, runs were performed as in Example 1, above, however, now using a reactor loaded only with packing materials, i.e., 30-50 mesh alpha-alumina and quartz wool.

Essentially no conversion of methane or oxygen was observed at 400° C. at 30-60 Ml/min feed rates.

Discussion

As essentially no conversion of methane or oxygen was observed in Example 2 using the same reactor but now loaded only with packing materials, the conversions observed in Example 1 are unaffected by wall effects.

Example 3

Deactivation of the crystalline copper aluminum borate catalyst was tested during a 19 hr run using a 2.5 g loading of the crystalline copper aluminum borate catalyst of Example 1 at 400° C. In addition, the same feed as used in Example 1 was used. A feed flow rate of 60 mL/min (0.094 WHSV methane) was used.

Discussion

At the initiation of the run, methane conversion was about 36% and oxygen conversion was about 69%. By the end of the 19 hr run, methane conversion had decreased to 31% and oxygen conversion had declined to 58%. The small declines in methane and oxygen conversion over the 19 hr run period, indicated a relatively low rate of onstream catalyst deactivation.

Example 4

A crystalline copper aluminum borate catalyst containing: a crystalline copper aluminum borate phase with a 2:3:2 $CuO:Al_2O_3:B_2O_3$ composition, an ICP Elemental Analysis of 21.6 wt. % copper, 28.1 wt. % aluminum, and 7.4 wt. % boron; and a BET (Digisorb) surface area of 131 $m^2/g$ prepared by the sol/gel technique described above, was prepared whereby the material was gelled by adding ammonium hydroxide and methanol to obtain a final pH of 8.2. The gel was dried and calcined for 4 hr at 760° C. The calcined material was ground and sieved to 20-35 mesh prior to testing for methane chlorination. The catalyst had the X-ray diffraction patterns shown in Table I and the significant X-ray diffraction lines set forth in Table A, above.

This catalyst was tested for methane chlorination by the procedure described above in Example 1. The results for a run at a temperature of 350° C. are given below in Table III.

TABLE II

| Run Temp (°C.) | Feed Rate (mL/min @ RT & 1 atm) | CH$_4$ WHSV (1/hr) | CH$_4$ Conv. | O$_2$ Conv. | Mole % Selectivities for Carbon-Containing Products | | | | | |
|---|---|---|---|---|---|---|---|---|---|---|
| | | | | | CH$_3$Cl | CH$_2$Cl | CHCl$_3$ | CCl$_4$ | CO | CO$_2$ |
| 350 | 90 | 0.071 | 10.7 | 7.1 | 100 | 0 | 0 | 0 | 0 | 0 |
| 350 | 60 | 0.047 | 9.6 | 9.4 | 97.1 | 2.9 | 0 | 0 | 0 | 0 |
| 350 | 30 | 0.024 | 14.7 | 20.6 | 78.6 | 7.0 | 0 | 0 | 14.3 | 0 |
| 375 | 90 | 0.071 | 14.7 | 19.2 | 66.3 | 15.1 | 0 | 0 | 16.3 | 2.3 |
| 375 | 60 | 0.047 | 15.4 | 26.8 | 62.7 | 16.3 | 0 | 0 | 18.4 | 2.6 |
| 375 | 30 | 0.024 | 24.6 | 46.6 | 51.7 | 20.3 | 0 | 0 | 23.2 | 4.8 |
| 400 | 90 | 0.071 | 25.2 | 40.5 | 57.3 | 17.7 | 2.4 | 0 | 19.8 | 2.9 |
| 400 | 60 | 0.047 | 34.3 | 60.4 | 46.9 | 20.8 | 3.9 | 0 | 24.4 | 4.1 |
| 400 | 30 | 0.024 | 39.6 | 100 | 35.8 | 21.8 | 5.2 | 0 | 26.8 | 10.3 |

TABLE III

| Feed Rate (mL/min) at RT & 1 atm | CH$_4$ Conv. | O$_2$ Conv. | Mole % Selectivities for Carbon-Containing Products | | | | | |
|---|---|---|---|---|---|---|---|---|
| | | | CH$_3$Cl | CH$_2$Cl$_2$ | CHCl$_3$ | CCL$_4$ | CO | CO$_2$ |
| 90 | 12.6% | 28.4% | 56.1 | 9.3 | 0 | 0 | 12.7 | 22.0 |
| 60 | 17.2% | 29.6% | 52.7 | 6.9 | 0 | 0 | 17.2 | 23.2 |

Discussion

As shown by the results in Table III, higher levels of methane and oxygen conversion were attained in Example 4 as compared to Example 1 (see Table II). Consequently, it may be concluded that if higher activity is desired, then higher surface area forms of the catalyst material may be preferred.

Example 5

Cu(NO$_3$)$_2$·5H$_2$O (232.7 g, 100. mol) dissolved in 200 mL warm deionized water, alumina sol (2218.4 g of 6.89 wt. % Al$_2$O$_3$ sol, 1.50 mol) and boric acid (124.1 g, 2.01 mol) dissolved in 600 mL warm deionized water were placed into a large Waring blender. After blending for several minutes, a thin gel formed having a pH of 3.3. A total of 1800 mL of a solution of 20% concentrated NH$_4$OH in methanol was added to the mixture. Subsequent blending resulted in a thick gel having a pH of 7.5 The material was placed on four 35×45 cm trays and allowed to air dry and subsequently dried in a vacuum oven at 0.3 atm and 120° C. for 17 hr in flowing nitrogen. Several batches were calcined with the following program:

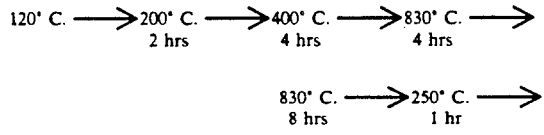

This preparation was repeated several times to obtain 143.6 g of product which was crushed and sieved to yield 20-35 mesh catalyst samples. The untreated catalyst had a BET surface area of 14 m$^2$/g, an ICP analysis of 19.8 wt. % copper, 22.6 wt. % aluminum, 7.4 wt. % boron, no detectable carbon, 0.06 wt. % hydrogen, 0.05 wt. % chlorine, and no detectable potassium and exhibited the X-ray diffraction patterns shown in Table I and the significant X-ray diffraction lines set forth in Table A, above.

Example 6

A 12.7 g sample of the 20-35 mesh copper aluminum borate prepared in Example 5 was impregnated with 1.27 g KCl dissolved in 75 mL deionized water by an incipient wetness method as follows: The KCl solution was added dropwise until an even wetness appeared. The material was allowed to dry overnight. The process was repeated 3 more times, and a final 3 mL rinse of the beaker was used for a last treatment. The material was treated at 400° C. for 6 hr. The resulting material, identified as Example 6, had a BET surface area of 10 m$^2$/g, an ICP analysis of 15.8 wt. % copper, 18.7 wt. % aluminum, 7.4 wt. % boron, 0.02 wt. % carbon, 0.09 wt. % hydrogen, 3.16 wt. % chlorine, and 3.07 wt. % potassium.

Example 7

A 13.2 g sample of the 20-35 mesh copper aluminum borate prepared in Example 5 was impregnated with 2.64 g KCl dissolved in 75 mL deionized water by an incipient wetness method as follows: the KCl solution was added dropwise until an even wetness appeared. The material was allowed to dry overnight. The process was repeated three more times, and a final 3 mL rinse of the beaker was used for a last treatment. Some white crystals appeared on the inside edge of the beaker, indicating that not all of the KCl was incorporated in the composition. The material was treated at 400° C. for 6 hr. The resulting material, identified as Example 7, had a BET surface area of 14 m$^2$/g, and an ICP analysis of 16.9 wt. % copper, 20.7 wt. % aluminum, 3.4 wt. % boron, 2.58 wt. % potassium, 3.46 wt. % chlorine and no detectable carbon or hydrogen.

Example 8

A 12.6 g sample of the 20-35 mesh copper aluminum borate prepared in Example 5 was impregnated with 1.26 g K$_2$CO$_3$ dissolved in 75 mL deionized water by an incipient wetness method as follows: the K$_2$CO$_3$ solution was added dropwise until an even wetness appeared. The material was allowed to dry overnight. The process was repeated three more times, and a final 3 mL rinse of the beaker was used for a last treatment. The material was treated in air at 600° C. for 6 hr. The resulting material, identified as Example 8, had a BET surface area of 9 m$^2$/g, and ICP analysis of 19.5 wt. % copper, 23.8 wt. % aluminum, 2.28 wt. % boron, 3.2 wt. % potassium, 0.74 wt. % chlorine and no detectable carbon or hydrogen.

Example 9

This example illustrates a comparison of the resulting catalyst of Examples 5-8 for catalytic activity in the chlorination of methane.

The catalyst testing apparatus of Example 1 was used.

Startup procedure entailed heating the catalyst charged reactor to a desired temperature and then starting a feed mixture flow, 90 mL/min measured at 1 atm and RT (corresponding to 0.071 hr$^{-1}$ methane WHSV). After 1.5-2 hr at operating conditions, a sample of reactor effluent gas was collected and GC-analyzed. Feed flow was then reduced to 60 mL/min (0.074 hr$^{-1}$ methane WHSV), and effluent was sampled after 1.5-2 hr. Feed rate was then reduced to 30 mL/min (0.024 hr$^{-1}$ methane WHSV), and effluent was sampled after 2-2.5 hr. After this sample was taken, feed was discontinued and the unit was purged with nitrogen flow overnight while raising the furnace temperature to the desired setting for the next run series.

Table IV presents the results of methane chlorination runs with the catalysts of Examples 5-8.

DISCUSSION

The data in Table IV illustrates that, at equivalent conversions of methane, selectivity to chloromethanes was significantly higher for potassium-containing copper aluminum borate catalysts than for comparable catalysts without potassium. Correspondingly, selectivity to carbon oxides was significantly reduced by the incorporation of potassium into the catalyst.

TABLE IV

Chlorination of Methane

| Conditions | | Conversions | | Selectivities | |
|---|---|---|---|---|---|
| T °C. | WHSV hr$^{-1}$ | Methane mole % | Oxygen mole % | Chlorocarbons mole % | Carbon Oxides mole % |
| Example 5 (Aqueous-Organic) | | | | | |
| 400 | 0.071 | 8.5 | 21.9 | 73.3 | 26.7 |
| 400 | 0.047 | 18.6 | 38.2 | 68.2 | 31.7 |
| 400 | 0.024 | 22.3 | 54.8 | 43.0 | 37.0 |
| 425 | 0.071 | 17.6 | 38.8 | 70.1 | 30.0 |
| 425 | 0.047 | 15.8 | 36.0 | 66.5 | 33.5 |
| 425 | 0.024 | 25.4 | 63.2 | 58.5 | 41.8 |
| Example 6 (Aqueous-Organic with 10% KCl) | | | | | |
| 400 | 0.071 | 4.7 | 11.7 | 87.7 | 12.3 |
| 400 | 0.047 | 11.1 | 19.7 | 80.3 | 19.7 |
| 400 | 0.024 | 18.8 | 34.8 | 79.6 | 20.4 |
| 425 | 0.071 | 13.9 | 22.6 | 81.7 | 18.3 |
| 425 | 0.024 | 43.7 | 50.1 | 80.6 | 19.4 |
| Example 7 | | | | | |
| 425 | 0.071 | 11.3 | 17.7 | 83.7 | 16.4 |
| 425 | 0.047 | 14.9 | 26.7 | 85.5 | 14.5 |
| 425 | 0.024 | 34.1 | 56.2 | 82.5 | 17.5 |
| Example 8 | | | | | |
| 400 | 0.071 | 8.9 | 16.8 | 76.6 | 23.4 |
| 400 | 0.047 | 15.1 | 22.9 | 80.0 | 20.0 |
| 400 | 0.024 | 20.7 | 42.3 | 80.4 | 19.6 |
| 425 | 0.071 | 16.7 | 29.2 | 83.8 | 16.2 |
| 425 | 0.047 | 19.3 | 36.4 | 82.1 | 17.9 |
| 425 | 0.024 | 31.9 | 63.6 | 79.7 | 20.3 |

It is to be understood that while the invention has been described above with reference to chlorination as the form of halogenation using the hydrogen halide, HCl (where "hydrogen halide" generally refers to HX, where X=F, Cl, Br and I), the invention, as identified above, is also believed to have applicability to hydrocarbon halogenation using other members of the halogen family, such as fluorine and iodine and, in particular, bromine and the corresponding hydrogen halide.

The foregoing detailed description is given for clearness of understanding only, and no unnecessary limitations are to be understood therefrom, as modifications within the scope of the invention will be obvious to those skilled in the art.

What is claimed is:

1. A method for halogenating hydrocarbons comprising the step of:
    contacting a reaction mixture comprising hydrocarbon-containing feed, a hydrogen halide and an oxygen-containing gas with a catalyst comprising crystalline copper aluminum borate under reaction conditions to form halogenated hydrocarbons.

2. The method of claim 1 wherein said crystalline copper aluminum borate has the following significant X-ray diffraction pattern and relative intensities:

| (d) Angstroms | Strength |
|---|---|
| 5.29 ± .05 | VS |
| 5.00 ± .05 | S |
| 3.73 ± .03 | W-M |
| 2.64 ± .03 | M-S |
| 2.61 ± .02 | W-M |
| 2.50 ± .02 | W-M |
| 2.26 ± .02 | W-M |
| 2.16 ± .02 | M |
| 2.07 ± .02 | M |
| 1.97 ± .02 | M |
| 1.86 ± .01 | W-M |
| 1.81 ± .01 | M | where VVS=very very strong (>100), VS=very strong (80–100), S=strong (50–80), M=medium (20–50), W=weak (10–20) and VW=very weak (<10).

3. The method of claim 2 wherein mole ratios of initial reactant concentrations for said crystalline copper aluminum borate is characterized by the general mixed oxide formula

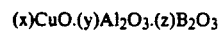

$$(x)CuO.(y)Al_2O_3.(z)B_2O_3$$

wherein x, y and z are numbers representing molar amounts of the respective oxides and wherein the mole ratios of $CuO/B_2O_3$, calculated as x/z, are about 0.1 to about 20 and the mole ratios of $Al_2O_3/B_2O_3$, calculated as y/z, are from about 0.1 to about 20.

4. The method of claim 1 wherein said halogenation comprises bromination and said hydrogen halide comprises HBr, wherein said halogenated hydrocarbons comprise brominated hydrocarbons.

5. The method of claim 1 wherein said catalyst additionally comprises a promoting amount of an alkali metal compound.

6. The method of claim 5 wherein the alkali metal of said compound is selected from the group consisting of lithium and potassium.

7. The method of claim 5 wherein said halogenation comprises chlorination and wherein said alkali metal compound is a nonchloride compound.

8. The method of claim 5 wherein said halogenation comprises chlorination and wherein said hydrocarbon-containing feed comprises lower hydrocarbons and wherein said chlorinated hydrocarbons comprise chlorinated lower hydrocarbons.

9. The method of claim 1 wherein said halogenation comprises chlorination and wherein said hydrocarbon-containing feed comprises lower hydrocarbons and wherein said chlorinated hydrocarbons comprise chlorinated lower hydrocarbons.

10. The method of claim 9 wherein said lower hydrocarbons comprise lower alkanes and said chlorinated lower hydrocarbons comprise chlorinated lower alkanes.

11. The method of claim 9 wherein said lower alkanes comprise methane and said chlorinated lower alkanes comprise chloromethane.

12. The method of claim 10 wherein said chloromethane comprises methyl chloride.

13. The method of claim 8 wherein said lower hydrocarbons comprise $C_2$ hydrocarbons and said chlorinated lower hydrocarbons comprise dichloroethane.

14. A method for chlorinating hydrocarbons comprising the step of contacting a reaction mixture comprising hydrocarbon-containing feed, HCl and an oxygen-containing gas under reaction conditions with a catalyst comprising crystalline copper aluminum borate, having the significant X-ray diffraction pattern and relative intensities:

| (d) Angstroms | Strength |
|---|---|
| 5.29 ± .05 | VS |
| 5.00 ± .05 | S |
| 3.73 ± .03 | W-M |
| 2.64 ± .03 | M-S |
| 2.61 ± .02 | W-M |
| 2.50 ± .02 | W-M |
| 2.26 ± .02 | W-M |
| 2.16 ± .02 | M |
| 2.07 ± .02 | M |
| 1.97 ± .02 | M |
| 1.86 ± .01 | W-M |
| 1.81 ± .01 | M | where VVS=very very strong (>100), VS=very strong (80-100), S=strong (50-80), M=medium (20-50), W=weak (10-20) and VW=very weak (<10).

to form chlorinated hydrocarbons.

15. The method of claim 14 wherein said catalyst additionally comprises a promoting amount of an alkali metal compound.

16. The method of claim 15 wherein the alkali metal of said compound is selected from the group consisting of lithium and potassium.

17. The method of claim 14 wherein said hydrocarbon-containing feed comprises lower hydrocarbons and said chlorinated hydrocarbons comprise chlorinated lower hydrocarbons.

18. The method of claim 17 wherein said lower hydrocarbons comprise lower alkanes and said chlorinated lower hydrocarbons comprise chlorinated lower alkanes.

19. The method of claim 18 wherein said lower alkanes comprise methane and said chlorinated lower alkanes comprise chloromethane.

20. The method of claim 19 wherein said chloromethane comprises methyl chloride.

21. The method of claim 17 wherein said lower hydrocarbons comprise $C_2$ hydrocarbons and said chlorinated lower hydrocarbons comprise dichloroethane.

22. A method for chlorinating methane comprising the step of contacting a reaction mixture comprising methane, HCl and an oxygen-containing gas under reaction conditions with a catalyst comprising crystalline copper aluminum borate and a promoting amount of alkali metal compound to form chloromethane, said crystalline copper aluminum borate having the following significant X-ray diffraction pattern and relative intensities:

| (d) Angstroms | Strength |
|---|---|
| 5.29 ± .05 | VS |
| 5.00 ± .05 | S |
| 3.73 ± .03 | W-M |
| 2.64 ± .03 | M-S |
| 2.61 ± .02 | W-M |
| 2.50 ± .02 | W-M |
| 2.26 ± .02 | W-M |
| 2.16 ± .02 | M |
| 2.07 ± .02 | M |
| 1.97 ± .02 | M |
| 1.86 ± .01 | W-M |
| 1.81 ± .01 | M | where VVS=very very strong (>100), VS=very strong (80-100), S=strong (50-80), M=medium (20-50), W=weak (10-20) and VW=very weak (<10).

and having a surface area in the range of about 0.1 to about 300 m²/g.

23. The method of claim 22 wherein the alkali metal of said compound is lithium.

24. The method of claim 23 wherein said alkali metal compound is a nonchloride compound.

25. The method of claim 22 wherein the alkali metal of said compound is potassium.

26. The method of claim 25 wherein said alkali metal compound is a nonchloride compound.

27. The method of claim 22 wherein said chloromethane comprises methyl chloride.

28. A method for chlorinating $C_2$ hydrocarbons comprising the step of contacting a reaction mixture comprising $C_2$ hydrocarbon-containing feed, HCl, and an oxygen-containing gas with a catalyst comprising crystalline copper aluminum borate, having the following significant X-ray diffraction pattern and relative intensities:

| (d) Angstroms | Strength |
|---|---|
| 5.29 ± .05 | VS |
| 5.00 ± .05 | S |
| 3.73 ± .03 | W-M |
| 2.64 ± .03 | M-S |
| 2.61 ± .02 | W-M |
| 2.50 ± .02 | W-M |
| 2.26 ± .02 | W-M |
| 2.16 ± .02 | M |
| 2.07 ± .02 | M |
| 1.97 ± .02 | M |
| 1.86 ± .01 | W-M |
| 1.81 ± .01 | M | where VVS=very very strong (>100), VS=very strong (80-100), S=strong (50-80), M=medium (20-50), W=weak (10-20) and VW=very weak (<10).

and having a surface area in the range of about 0.1 to about 300 m²/g to form a product mixture comprising dichloroethane.

29. The method of claim 28 wherein said catalyst additionally comprises a promoting amount of an alkali metal compound.

30. The method of claim 29 for alkali metal of said compound is selected from the group consisting of lithium, potassium and combinations thereof.

* * * * *